US 6,495,107 B2

(12) United States Patent
Gaines

(10) Patent No.: US 6,495,107 B2
(45) Date of Patent: Dec. 17, 2002

(54) INCENSE BURNER

(76) Inventor: G. David Gaines, 92 Albury Way, North Brunswick, NJ (US) 08902

( * ) Notice: Subject to any disclaimer, the term of this patent is extended or adjusted under 35 U.S.C. 154(b) by 109 days.

(21) Appl. No.: 09/855,940

(22) Filed: May 15, 2001

(65) Prior Publication Data

US 2002/0172623 A1 Nov. 21, 2002

(51) Int. Cl.⁷ .................................................. A61L 9/02
(52) U.S. Cl. ........................ 422/124; 422/126; 422/306
(58) Field of Search ................................. 422/124, 126, 422/305, 306

(56) References Cited

U.S. PATENT DOCUMENTS

| 1,969,756 A | 8/1934 | Lowell |
| 4,154,251 A | 5/1979 | Doyel |
| 4,155,979 A * | 5/1979 | Powell ........................ 422/126 |
| 4,219,531 A | 8/1980 | Wisniewski |
| 5,215,719 A | 6/1993 | Newman |

FOREIGN PATENT DOCUMENTS

JP 04229501 A * 8/1992

* cited by examiner

Primary Examiner—Robert J. Warden, Sr.
Assistant Examiner—Sean E. Conley
(74) Attorney, Agent, or Firm—Daniel S. Kirshner

(57) ABSTRACT

An incense burner comprising a base portion and a removable tapered stack portion and which includes an electric fan to disperse incense smoke. The base portion defines a fan retention cavity configured to retain the electric fan. Attached to the top of the electric fan is a vented platform containing a plurality of vents and an incense retainer aperture. An incense retainer retains an ignited stick of incense and is positioned into the incense retainer aperture. A tapered stack which includes a smoke retardant ring is removably positioned on top of the vented platform. The electric fan is switched on thereby causing the incense smoke to present itself in a pleasing manner.

13 Claims, 3 Drawing Sheets

INCENSE BURNER

FIELD OF THE INVENTION

The present invention relates generally to incense holders and burners and more specifically to an incense burner that includes a removable tapered smokestack and an electric fan to disperse incense smoke in an advantageous and pleasing manner.

BACKGROUND OF THE INVENTION

Burning incense is popular in order to provide a pleasant aroma, create a particular atmosphere, or to mask unpleasant or undesirable odors. An examination of the prior art in the field of incense burners reveals several devices, none of which exhibit the novel combination of elements that are disclosed by the present invention. Typical prior art incense burners include a retaining element for securing an ignited piece of incense and means for catching falling incense ash.

It is known in the art to include a fan element for dispersing incense smoke throughout the room in which the incense is being burned. For example, U.S. Pat. No. 4,219,531 entitled Smoke Diffusing Device issued to Wisniewski on Aug. 26, 1980 discloses such a device.

It is also known in the art to provide a cylindrical smoke stack or chimney device to surround a lit stick of incense. Such an incense burning device is disclosed in U.S. Pat. No. 5,215,719 entitled Incense Burner issued to Newman on Jun. 1, 1993. Another such device is shown in U.S. Pat. No. 4,155,979 issued to Powell on May 22, 1979 which discloses a Combination Incense Burner and Incense Storage Device.

None of the prior art discloses a device that causes the incense smoke to present a visual display before being dispersed throughout a living space. It would be advantageous to offer a variation on a device which historically appeals to one human sense (smell) and double the number of senses effected by adding a visual spectacle. More specifically, it would be advantageous to provide a device for retaining and burning incense that will cause the incense smoke to gather, linger and undulate in the vicinity of the device. This present invention is just such a device which includes a means for retaining a burning piece of incense, means for impelling air flow through the incense burner, and means for dispersing the incense smoke in a visually pleasing manner. None of the prior art includes a fan element combined with a removable chimney that includes a smoke-retardant ring. Such are the objectives, advantages and novel structural elements presented by the invention disclosed herein.

Other objectives, advantages and novel features, further scope of applicability of the present invention will be set forth in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

SUMMARY OF THE INVENTION

The present invention incense burner is a device for retaining and burning incense in such a manner that the smoke becomes subjected to the laws of physics which, until now, had not been harnessed for this purpose. The incense burner comprises generally a base member and a tapered stack. Within the base member, a fan retention unit defines a fan retention cavity. A switched electric fan unit is provided which is positioned inside of the fan retention cavity. Attached to top of the electric fan is a vented platform which contains a plurality of vents and an incense retainer aperture. An incense retainer is provided to hold a standard stick of incense which takes the form of a tapered shaft with a washer or disc attached thereto and which is configured to fit into the incense retainer aperture. A retainer guard in the form of a hexagonal nut surrounded by a metal foundation ring which is in turn surrounded by a circular rubber member forms a receptacle to receive falling ashes and embers. The fan retention unit sits on top of a four tiered rubber gasket, which in turn rests on a base with a dynamic aperture. A tapered stack or chimney is removably positioned on the top of the vented platform. The stack tapers from bottom to top and at its top includes a smoke-retardant ring and may have a screwably removable top portion. At the bottom of the stack and positioned amid its four legs is an air flow inhibitor.

The invention is employed by lighting a stick of incense and placing it into the incense retainer. The incense retainer is placed into the incense retainer aperture on the vented platform and the retainer guard is positioned around the incense retainer. Now the tapered stack is placed around the ignited stick of incense thereby surrounding it. The unit is plugged into an electrical outlet and the fan is switched on. Thus, air is sucked through the bottom of the device, through the fan cavity, through the vented platform and through the tapered stack where it mixes with incense smoke. The smoke traverses the tapered stack where it exits over the smoke-retardant ring. As such, the smoke presents itself in a pleasing manner, lingering and dispersing, due to the conflicting upward and downward air drafts.

BRIEF DESCRIPTION OF THE DRAWINGS

For a better understanding of the present invention, reference is made to the following description of an exemplary embodiment thereof, considered in conjunction with the accompanying drawings, in which.

DETAILED DESCRIPTION OF THE INVENTION

Figure 1:
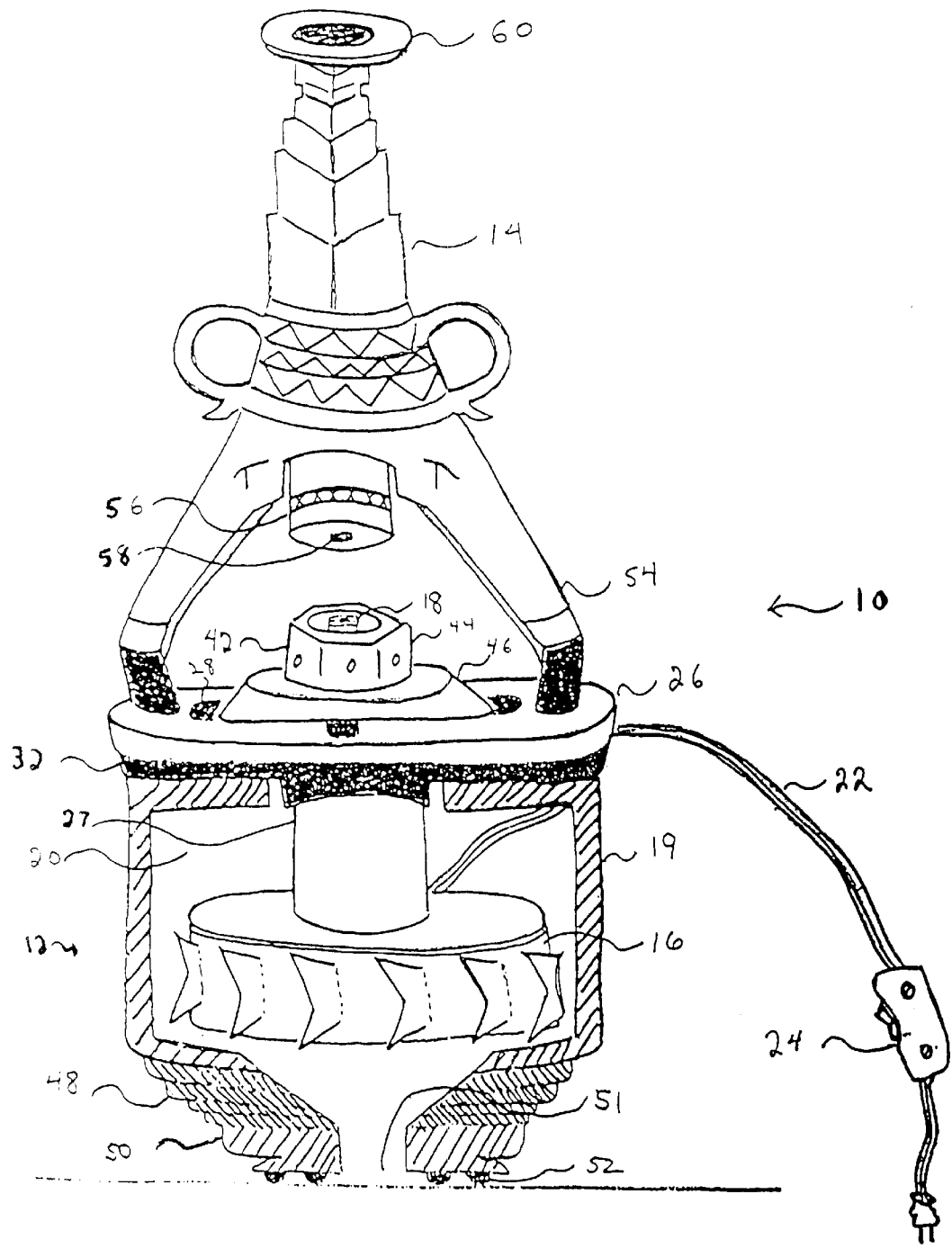
FIG. 1 is a side perspective view of the present invention incense burner showing the fan cavity in cross section, thereby revealing the fan contained therein.

Referring to FIG. 1, the present invention is an incense burner 10 designed to retain an ignited piece of incense and to disperse the smoke therefrom in an aesthetically pleasing and aromatically desirable manner. Generally, the incense burner 10 comprises a base portion 12 and a separate removable tapered stack portion 14.

Figure 3:
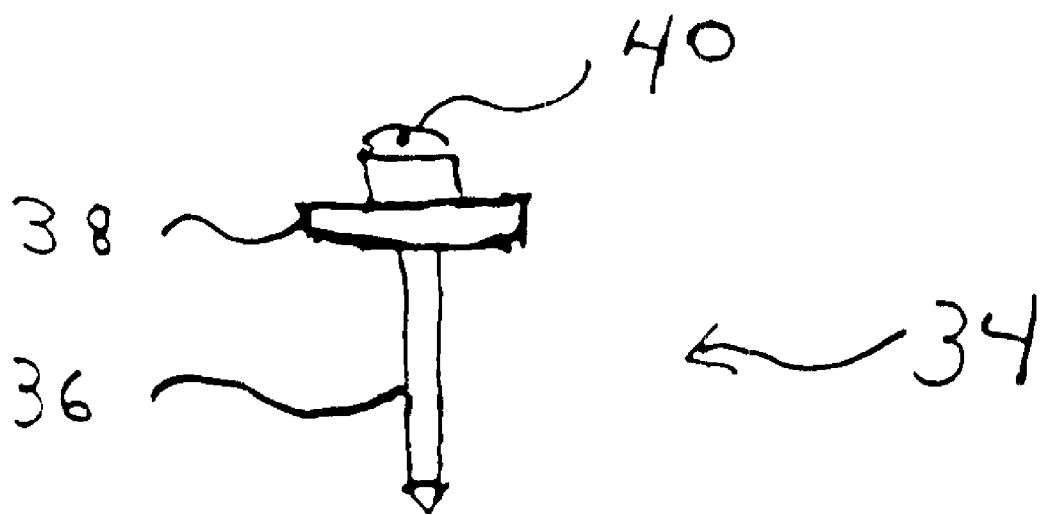
FIG. 3 is a side elevational view of the incense retainer of the present invention.

First, we turn our attention to the base unit 12 which is configured to house an electric fan unit 16 and an incense retainer 18 which is shown in greater detail in FIG. 3. The electric fan 16 is housed in a fan retention member 19 which is formed as a metallic cylindrical tube defining a fan retention cavity 20 therein. Although the particular composition of the fan retention member 19 is not critical, the dimensions are important. Specifically, the interior dimension of the fan retention member which is designated as the fan cavity 20 should be just large enough to encompass the blades of the fan 16 without hindering free rotation of the blades of the fan. More specifically, the blades of the fan should be separated from the structure wall by a distance of approximately ³⁄₁₆". In embodiment shown in FIG. 1, the distance between the bottom of the fan and fan cavity's bottom wall should be approximately ³⁄₁₆".

An electric fan 16 is provided and positioned into the fan cavity 20. In the embodiment shown, the electric fan is a standard, off-the-shelf, 110–120 watt equipment cooling fan which is designed for the cooling of industrial equipment. The fan blades and rotating hub are fashioned from plastic and situated below its motor component. The motor component contains at its center an opening for the application of lubricant. Two aluminum electrical wires 22 exit the fan's motor component, each enrobed in its own plastic sleeve. In the embodiment shown, these aluminum wires are spliced into a 16 gauge extension cord containing copper wires. A standard, off-the-shelf electrical on/off remote switch 24 is wired into the electric cord. It should be appreciated that another embodiment in which the electric switch 24 is located on the base 12 of the incense burner is well within the scope of this disclosure.

Figure 2:
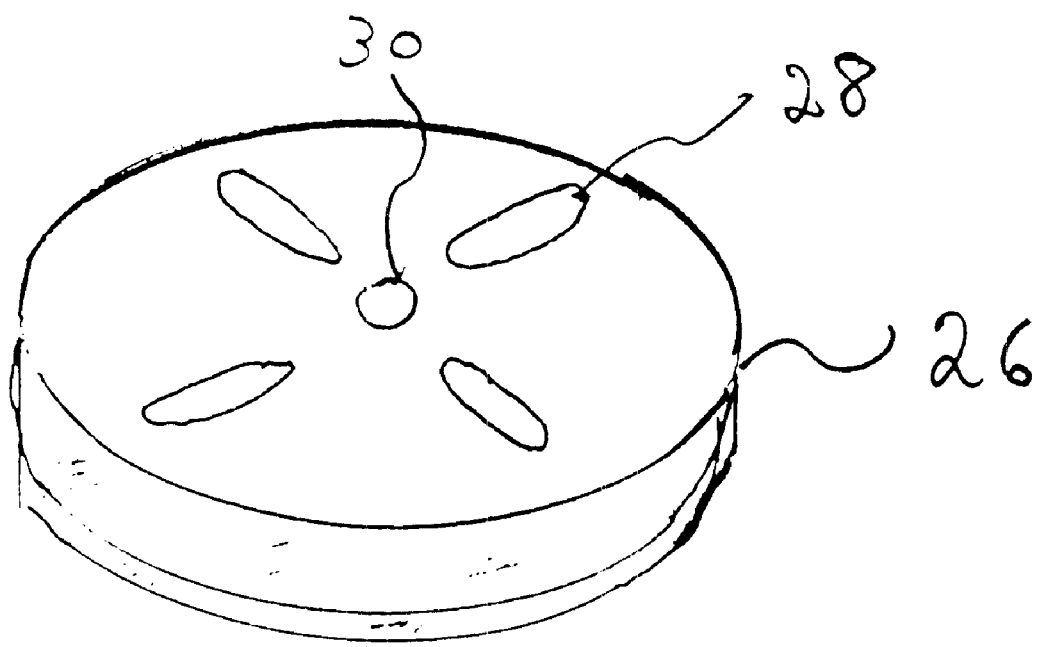
FIG. 2 is a top elevational view of the vented platform of the present invention.

Firmly attached to top of the electric fan 16 is a vented platform 26 whose embodiment is shown in greater detail in FIG. 2. The vented platform is attached to the top of the electric fan by means of a hollow cylindrical extension denoted 27. The hollow cylindrical extension which connects the electric fan and the vented platform allows a user to introduce lubrication to the fan and provides the necessary distance between the fan and the vented platform. Specifically, the distance between the top surface of the fan's motor component and the top surface of the vented platform should be approximately 1.25 inches when utilizing an 80 watt fan. The vented platform 26 is a thick steel or metal circular disc of a diameter similar to the exterior diameter of the fan retention member 19. Four oblong air vents 28 are formed into the vented platform which permit the circulation of air from the fan unit 16. The four air vents 28 are equidistant from the center of the vented platform and equidistant from each other. At the center of the vented platform is located a circular aperture 30 which serves two purposes. First, the circular aperture 30 will operate to receive the incense retainer (to be described in greater detail later). Second, the circular aperture serves as access for the purpose of introducing lubricant to the electric fan attached thereto. The vented platform and the connected fan are removable from the fan retention member 19.

Referring back to FIG. 1, a rubber gasket 32 is attached to the hollow cylindrical extension 27 and is situated between the vented platform 26 and the upper rim of the fan retention member 19. The rubber gasket 32 has a diameter that approximates that of the vented platform and the exterior diameter of the fan retention member. Vents (not shown) are cut into the rubber gasket wherein such vents are of a size, position and configuration to coordinate with the oblong vents 28 on the vented platform 26 to permit the free flow of air therethrough. The rubber gasket serves the purpose of sealing air flow from the exterior while allowing free air flow through the interior of the device through its vents. The rubber gasket also acts as a buffer, eliminating friction between steel and metal parts that would otherwise not rest against one another firmly.

Referring to FIG. 3, an incense retainer 34 is provided for the retention of a standard stick of incense. In its present embodiment, the incense retainer 34 includes an elongated shaft 36 made from brass or other metal which tapers to a point at one end. The overall length of the incense retainer is approximately 1.75 inch. As the incense retainer 34 will be placed into the circular aperture 30 on the vented platform 26, it should be appreciated that the diameter of the shaft 36 of the incense holder must be smaller than the diameter of the circular aperture 30 as to accommodate introduction of the shaft thereto. A metal disc or washer 38 is secured to the shaft 36 of the incense retainer and affixed thereto so that the diameter of the washer is perpendicular to the longitudinal axis of the shaft 36. The diameter of the washer 38 must be larger than the diameter of the circular aperture 30 of the vented platform. Thus, the shaft 36 of the incense retainer may be introduced into the circular aperture 30 until its progress is impeded by the abutment of the washer 38 against the vented platform 26. At the end of the shaft opposite the tapered end, there is provided an incense stick retaining hole 40, of a circular dimension appropriate to firmly retain a standard stick of incense.

A retainer guard 42 is provided which rests on top of the vented platform 26. In the present embodiment, the retainer guard 42 is formed from metal and rubber. As seen in FIG. 1, the retainer guard 42 includes a metallic hexagonal nut 44 which is surrounded by a metal foundation ring which is, in turn, surrounded by a circular rubber member 46. (The circular rubber member is a stretch-fit rotary shaft seal.) In the preferred embodiment shown, the retainer guard 42 has a height just taller than the top of the incense retainer 18. As is evident, the overall circular dimension of the rubber member must be small enough so that the oblong air vents 28 on the vented platform are only partially obstructed. The retainer guard 42 serves multiple purposes. First, it forms a cup of sorts to receive falling ashes and debris. Second, the retainer guard optimizes the flow of air through the device which contributes to the overall success of the system.

The fan retaining member 19 rests on top of a gradational spacer 48 formed from rubber. The rubber gradational spacer 48 is formed as four round gasket rings which decrease in diameter from top to bottom. The topmost and largest of the four rings lies flush against the bottom surface of the fan retaining member 19. The center, hollow channel of the four rings presents a channel through which air can be drawn up from the bottom of the incense burning device thereby facilitating circulation therethrough.

Finally, the rubber gradational spacer 48 sits on top of a base 50 which has a dynamic aperture 51. The base 50 is formed from a large OD raised washer, made of malleable iron, whose diameter is substantially similar to the bottom of the rubber gradational spacer 48. The dynamic aperture, as seen in FIG. 1, is a hole located at the center of the base 50, and is critical to operation of the system as it allows air to be drawn up into the system to be mixed with incense smoke. The size of the dynamic aperture effects the extent to which the air within the system is downwardly drawn. In other words, if this hole were closed, air would only be drawn upward, thus negating the aesthetic superiority of the system. If the hole were too large, it would cause the stick of incense to be snuffed out because too large a hole will cause much of the oxygen to be sucked out of the system. Specifically, to optimize performance of the system, the distance between the dynamic aperture and the bottom-most surface of the fan should be approximately 0.90625". The diameter of the dynamic aperture should be approximately 0.65625". These measurements are optimized when the fan employed is an 80 watt fan. The dimensions could change if a fan of a different wattage were utilized. Four raised rubber stabilizers 52 are attached to the bottom surface of the base 50. The stabilizers 52 will reduce any cumulative wear which might result from the slight vibrations produced by the fan. More importantly, the rubber stabilizers create a wafer thin layer of air between the device and the surface upon which it rests, so that the air can be drawn up into the system.

Now, we turn our attention to a description of the tapered stack 14. The tapered stack is formed like a chimney and takes the shape of a vertical, metallic pipe that tapers from bottom to top and then widens again at its top. The height of the tapered stack is not critical so long as it is taller than a stick of incense. During operation of the system, the tapered stack surrounds a stick of incense and acts as both a channel and containment chamber for the incense smoke. The tapered stack is supported by four slightly bent legs 54 whose feet are fashioned from rubber. During operation of the system, the tapered stack rests with its four feet sitting on top of the vented platform 26. It should be appreciated that the tapered stack is a separate entity from the base unit 12, merely resting on the vented platform. As such, it is readily removable from the base unit. The uppermost section of the tapered stack may be screwably removable to make the tip of a stick of incense easily accessible for lighting.

Connected to the underside of the tapered stack and centered amid the four legs thereof, is an air flow inhibitor 56. The air-flow inhibitor is a stout metallic cylinder exhibiting thick walls and a meager inner diameter and including a hollow central doughnut hole 58. As such, the air-flow inhibitor serves as a suitable receptacle for a stick of incense. Additionally, the air-flow inhibitor regulates the intake of forced air therethrough thereby allowing the smoke to escape at a leisurely pace.

Fitted to the apex of the tapered stack is a smoke-retardant ring 60. This flat, metallic, washer-like ring has a diameter greater than that of the rest of the tapered stack. The smoke-retardant ring is attached so that its diameter is perpendicular to the longitudinal axis of the tapered stack. The smoke-retardant ring delays the dissipation of smoke, causing it to gather, linger and traverse the top surface thereof The present invention operates in the following manner: A stick of incense is lit and inserted into the incense stick retaining hole 40 of the incense retainer 34. Thereafter, the tapered end of the incense retainer which is holding the ignited stick of incense is inserted into the circular aperture 30 on the vented platform. It will be appreciated that the stick of incense is now positioned upright and extending upward from the vented platform 26. The retainer guard 42 is positioned around the incense retainer. Now, the tapered stack 14 is positioned onto the vented platform with its four feet resting on the vented platform 26 in such a position so that the oblong vents 28 are not obscured. Specifically, the lit piece of incense is fed through the air flow inhibitor 56 so that the ignited stick of incense is surrounded by the tapered stack. More specifically, the stick of incense is positioned through the doughnut hole 58 of the air-flow inhibitor 56 and into the interior of the tapered stack 14. Once the tapered stack is placed into position, the unit is plugged into an electrical outlet and switched on. In the embodiment of the invention that includes a screwably removable top portion of the tapered stack, one is able to ignite the stick of incense after everything has been positioned leaving only the task of re-screwing the tapered stack back together after the stick has been lit.

Due to the action of the fan, air is drawn up into the system, and because of the dynamic aperture 51, the air is also drawn downwardly. Air is drawn up from the bottom through the base and then enters into the fan retaining chamber 20 where it is blown up through the vents 28 of the vented platform 26. Next the air is forced into the tapered stack 14 where it mixes with incense smoke. Finally, the smoke extends out of the tapered stack over the smoke-retardant ring 60. It will be understood that due to the interaction of the elements of the device, the smoke lingers and escapes at a leisurely pace. Specifically, the advantageous interaction of the parts of the invention produce the following phenomenon: Two forcibly produced and conflicting currents of air, one upwardly agitated and the other downwardly drawn, each struggling to dominate the other within a confined space.

What is claimed is:

1. An incense burner comprising:
   a base, said base forming a hollow cavity;
   a fan unit contained within said hollow cavity on said base;
   an incense retaining element;
   a chimney having an upper edge, said chimney removably resting on said base, whereby
   said chimney surrounds a piece of incense; and
   a smoke retardant ring attached to said upper edge of said chimney.

2. The incense burner of claim 1 wherein said fan unit includes a switch to turn said fan on and off.

3. The incense burner of claim 1 wherein said chimney is tapered.

4. The incense burner of claim 1 wherein said chimney includes feet.

5. The incense burner of claim 4 wherein said chimney includes four feet.

6. The incense burner of claim 1 which further includes a vented platform attached to said fan unit.

7. The incense burner of claim 1 which further includes a retainer guard.

8. The incense burner of claim 7 where said retainer guard comprises a hexagonal nut surrounded by a circular rubber member.

9. The incense burner of claim 1 where said chimney includes an air flow inhibitor.

10. The incense burner of claim 9 wherein said air flow inhibitor is a hollow cylinder.

11. The incense burner of claim 1 wherein said chimney has a removable top section.

12. An incense burner comprising:
    means for retaining a piece of incense;
    a removable chimney, said chimney serving to surround the piece of incense and having an upper edge wherein said chimney includes a smoke retardant ring at said upper edge of said chimney; and
    means for forcing a flow of air through said chimney thereby dispersing smoke from the burning incense.

13. The incense burner of claim 12 wherein said means for forcing air through said chimney is an electric fan.

* * * * *